(12) United States Patent
Muth

(10) Patent No.: US 8,796,893 B2
(45) Date of Patent: Aug. 5, 2014

(54) APPARATUS WITH A DIRECTLY DRIVEN ROTATING BODY AND AEROSTATIC BEARINGS

(75) Inventor: Michael Muth, Munich (DE)

(73) Assignee: AeroLas GmbH Aerostatische Lager-Lasertechnik, Unterhaching (DE)

( * ) Notice: Subject to any disclaimer, the term of this patent is extended or adjusted under 35 U.S.C. 154(b) by 1308 days.

(21) Appl. No.: 12/376,562

(22) PCT Filed: Aug. 10, 2007

(86) PCT No.: PCT/EP2007/007098
§ 371 (c)(1),
(2), (4) Date: Jun. 24, 2010

(87) PCT Pub. No.: WO2008/017498
PCT Pub. Date: Feb. 14, 2008

(65) Prior Publication Data
US 2010/0254640 A1    Oct. 7, 2010

(30) Foreign Application Priority Data

Aug. 10, 2006   (DE) .......................... 10 2006 037 543

(51) Int. Cl.
*A61B 6/00* (2006.01)
*A61B 6/03* (2006.01)
*F16C 32/06* (2006.01)
*H02K 7/08* (2006.01)

(52) U.S. Cl.
USPC ....... 310/90; 310/67 R; 310/156.01; 378/131; 378/132; 384/107; 384/122

(58) Field of Classification Search
CPC ...................................... F16C 32/06
USPC ............ 310/90, 156.01, 156.04, 268, 156.32, 310/156.36, 67 R; 378/131, 132; 384/107, 384/122
See application file for complete search history.

(56) References Cited

U.S. PATENT DOCUMENTS

| | | | |
|---|---|---|---|
| 2,993,159 A * | 7/1961 | Devol | 318/400.39 |
| 3,351,394 A | 11/1967 | Hooker | |
| 3,982,796 A * | 9/1976 | Hill | 384/307 |
| 4,081,707 A * | 3/1978 | Hartl et al. | 378/132 |

(Continued)

FOREIGN PATENT DOCUMENTS

| | | |
|---|---|---|
| DE | 31 25 740 A1 | 1/1983 |
| DE | 38 15 029 A1 | 11/1989 |

(Continued)

*Primary Examiner* — Burton Mullins
(74) *Attorney, Agent, or Firm* — Kilpatrick Townsend & Stockton LLP

(57) ABSTRACT

A device having a directly driven rotating body (1), its circumference (11) being radially seated on radial bearings (4, 4') in relation to the stationary body (2), and its at least one first face side (10) being axially seated in relation to the stationary body (2), wherein aerostatic bearings (5, 5', 5") are provided for the axial support mounting, characterized in that the first face side (10) has an annular magnet arrangement (32), which is configured coaxially to the axis of rotation (X) of the rotating body (1), and that the stationary body (2) has at least one electric coil arrangement (30), which is located opposite the annular magnet arrangement (32) in the axial direction and which forms together with the annular magnet arrangement (32) the components of an electrical direct drive (3) for the rotating body (1).

16 Claims, 2 Drawing Sheets

(56) References Cited

U.S. PATENT DOCUMENTS

| | | | |
|---|---|---|---|
| 4,942,597 A * | 7/1990 | Van Acker et al. | 378/197 |
| 4,958,098 A * | 9/1990 | Sarraf | 310/156.32 |
| 5,268,955 A * | 12/1993 | Burke et al. | 378/135 |
| 5,608,771 A | 3/1997 | Steigerwald et al. | |
| 5,645,354 A * | 7/1997 | Heinzl et al. | 384/100 |
| 6,327,340 B1 * | 12/2001 | Runnoe | 378/130 |
| 6,590,953 B2 * | 7/2003 | Suzuki et al. | 378/15 |
| 6,876,122 B2 | 4/2005 | Hansen | |
| 7,238,066 B2 * | 7/2007 | Taylor et al. | 440/38 |
| 7,352,096 B2 * | 4/2008 | Dunn et al. | 310/156.43 |
| 2004/0017895 A1 | 1/2004 | Suzuki et al. | |
| 2004/0062356 A1 | 4/2004 | Brunnett | |
| 2005/0116558 A1 | 6/2005 | Yokoyama et al. | |
| 2007/0046131 A1 * | 3/2007 | Boebel et al. | 310/216 |
| 2010/0007225 A1 * | 1/2010 | Platon et al. | 310/45 |

FOREIGN PATENT DOCUMENTS

| | | |
|---|---|---|
| DE | 44 36 156 C1 | 3/1996 |
| DE | 197 45 216 A1 | 5/1999 |
| DE | 100 26 752 A1 | 12/2001 |
| DE | 602 07 851 T2 | 8/2006 |
| EP | 0 023 657 A1 | 2/1981 |
| EP | 0 158 051 A1 | 10/1985 |
| EP | 0 215 523 A1 | 3/1987 |
| WO | WO 02/089671 A2 | 11/2002 |
| WO | WO 2005/102171 A1 | 11/2005 |
| WO | WO 2006/089741 A1 | 8/2006 |

* cited by examiner

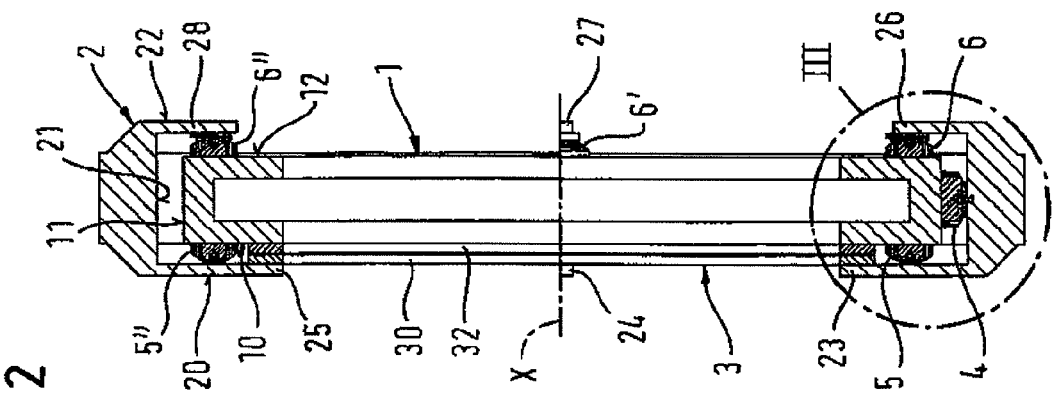
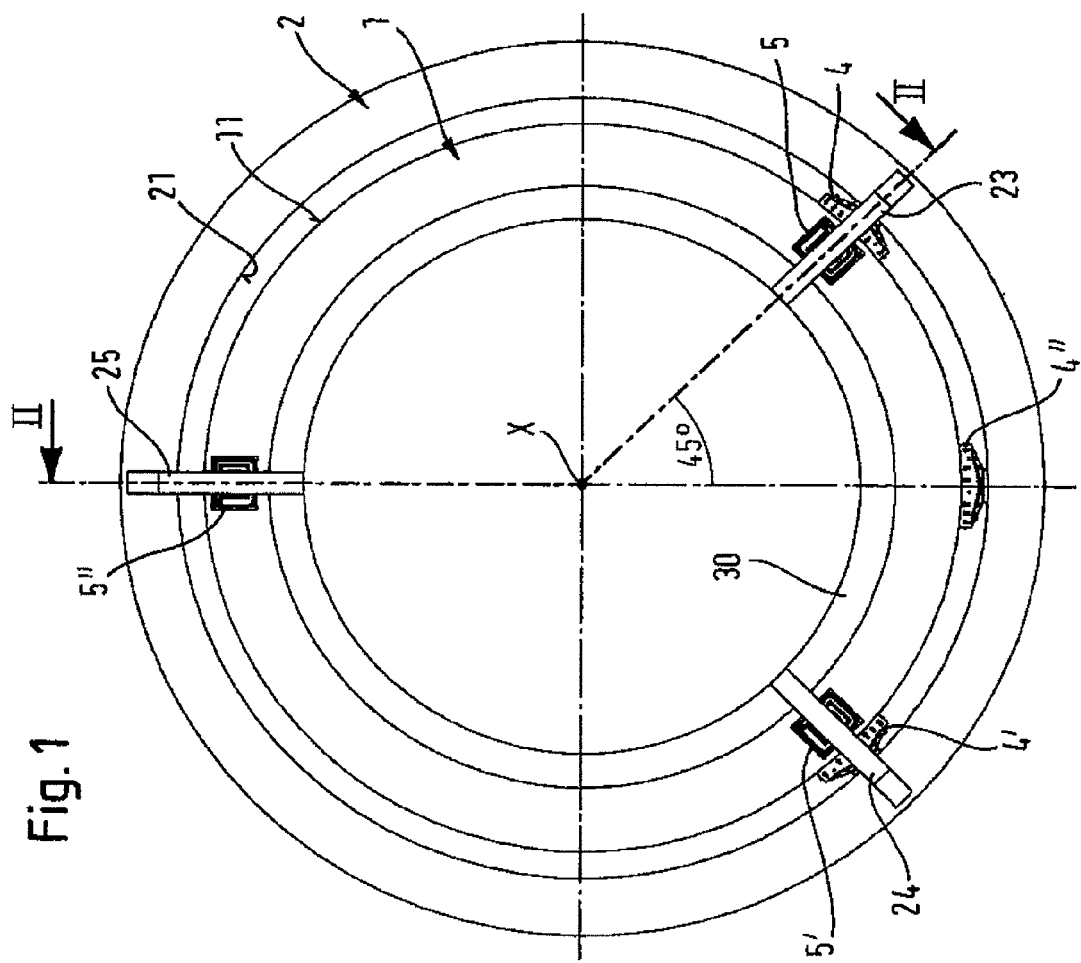

APPARATUS WITH A DIRECTLY DRIVEN ROTATING BODY AND AEROSTATIC BEARINGS

RELATED APPLICATIONS

This application claims the priorities of German Patent Application No. 10 2006 037 543.2 filed Aug. 10, 2006 and of PCT Application No. PCT/EP/2007/007098 filed Aug. 10, 2007, the disclosures of which are incorporated herein by reference.

BACKGROUND OF THE INVENTION

The invention relates to an apparatus having a directly driven rotating body in accordance with the preamble of claim 1 and to an aerostatic bearing in accordance with the preamble of claim 12.

Such devices are known from WO 02/089671 A2, which discloses an aerostatic rotor bearing for the rotating annular gantry of a computed tomography (CT) scanner. The construction of such CT scanners is generally known, for example, from that document. The disclosure of WO 02/089671 A2 is explicitly referred to herein with respect to the construction of a CT scanner, and its disclosure is incorporated herein by reference.

An imaging apparatus is typically mounted on the annular gantry of a CT scanner, and the imaging apparatus rotates about an area to be examined together with the annular gantry.

In order to clearly image moving bodies, for example a heat beating during examinations with a CT scanner, it is necessary for the rotating gantry to rotate at a sufficiently high speed and to be precisely guided. However, the required high speed can no longer be achieved with systems that are seated on roller bearings due to the required large diameter of the gantry and the resulting high peripheral speed of the bearing bodies. For this reason the device disclosed in WO 02/089671 A2 uses aerostatic bearings.

For aerostatic bearings to function reliably, it is necessary to keep the gap between the opposite bearing surfaces small. Hence, the distance between the opposite bearing surfaces is very small.

Due to the large diameter of the gantry and the asymmetrically mounted imaging equipment, deformations of the annular gantry are encountered, especially at high speeds, so that a predefined size of the bearing gap over the entire rotation of the annular gantry is not guaranteed. Although WO 02/089671 A2 teaches that at least some of the aerostatic bearings are adjustable in order to accurately adjust the air gap, this approach does not allow the deformations of the rotor to be balanced. In particular, when the annular gantry is directly driven, it may lead to alternating magnetic radial forces due to the magnetic forces of the drive that act between the stationary body and the rotating gantry. These magnetic radial forces produce further zonal deformations of the annular rotating gantry and, in addition, induce a dynamic imbalance, which can also be called the "magnetic imbalance", which cannot be balanced with the adjustable bearings of WO 02/089671 A2.

BRIEF SUMMARY OF THE INVENTION

It is therefore an object of the present invention to provide a device as generally described above that significantly reduces the effects of a "magnetic imbalance" on the directly driven rotating body and that permits rotational speeds that are higher than what could be attained in the past.

A further object of the invention is to provide an aerostatic bearing that also makes it possible to achieve the aforementioned object.

The device-related object is attained with the features disclosed in patent claim 1.

By providing the electrical direct drive with its annular magnet arrangement and annular coil arrangement on a face side of the rotating body, the magnetic field lines between the magnet arrangement and the coil arrangement and, thus, the attractive forces, acting between these two components of the electrical direct drive, run in the axial direction, and not in the radial direction as in the case of conventional CT scanners. As a result, changes in the magnetic forces of this drive do not result in local radial changes of the rotating body. Instead, they only result in a local deformation of the rotating body in the axial direction. Consequently the peripheral contour of the rotating body remains essentially constant during its rotation. Hence, there are no deformations and/or "magnetic imbalances" that act in the radial direction, and the radial bearings form an average distance between the bearing surfaces that is essentially constant during the rotation of the rotating body. This guarantees that the radial bearings will function reliably, especially when they are configured as aerostatic bearings.

In particular, the radial bearings are also aerostatic bearings to achieve an almost frictionless fit of the rotating bodies in the radial bearings.

A preferred embodiment of the present invention provides that the second face side, which faces away from the first face side of the rotating body, is assigned at least one additional aerostatic axial bearing that has at least one bearing pad which can be moved in a direction parallel to the axis and that is prestressed against the second face side of the rotating body by means of a spring force, a pneumatic force or a hydraulic force and forms an axial balancing bearing. In this way the rotating body is seated in an effectively floating manner in the axial direction between the bearings, which are arranged on the two face sides of the rotating body, so that the bearing(s) provided on the second face side with the movable bearing pad produce(s) not only a prestress of the respective axial bearings, but also an axial displacement of the respective bearing area of the respective bearing pad assigned to the second face side. In this way it is possible to geometrically balance local axial deformations of the rotating body that are generated by the "magnetic imbalance" because the bearing pad can conform in the axial direction to the local cyclic displacement of the rotating body.

Preferably at least one additional aerostatic radial bearing is provided below the rotating body. This additional aerostatic radial bearing has at least one bearing pad that can be moved in the radial direction and that pushes against the outer periphery of the rotating body by means of a spring force, a pneumatic force or a hydraulic force. This radial balancing bearing offers the same fundamental advantages as the above-described axial balancing bearings.

Preferably the first face side of the rotating drive is provided with at least one additional aerostatic axial bearing that has at least one bearing pad that is movable in a direction parallel to the axis and that is prestressed against the first face side of the rotating body by means of a spring force, a pneumatic force or a hydraulic force. This additional axial bearing with the movable bearing pad on the first bearing side increases the load carrying capacity of the bearings assigned to the first face side without, however, impairing the static certainty of the mounting support that is defined by preferably three aerostatic bearings that provide for the axial mounting support without resulting in a static over-redundancy of this mounting support.

It is especially advantageous if at least one part of the axial bearings has at least one swivelable bearing pad that can be swiveled about a first axis that runs perpendicular to the axis of rotation of the rotating body. Such a swivelable bearing pad makes it possible to compensate for unequal loads on the bearing pad generated by aerodynamic forces arising at the region of the bearing while the rotating body rotates.

It is particularly advantageous that the respective swivelable bearing pad can also be swiveled about a second axis that runs perpendicular to a plane spanned by the first axis and the axis of rotation.

It is especially advantageous to provide the swivelable bearing pad with a ball head bearing that is configured to be freely swivelable.

This swivel capability of the bearing pad about one axis, about two axes that are at right angles to each other, or even about a center point of a sphere, is also attained in an advantageous manner with the radial bearings.

It is especially advantageous if the respective bearing pads are configured in such a manner that the bearing capacity of the bearing increases in the movement direction of the opposite bearing surface moving past the bearing pad. In this way the relatively inclined position assumed by the bearing caused by the aerodynamic effects, which results in bearing surfaces positioned in relation to each other so that they form a bearing gap that is wedge-shaped in cross-section, can be compensated by varying the load bearing capacity over the longitudinal extent of the bearing pad.

Such a bearing capacity which changes over the longitudinal extent of the bearing is advantageously attained with a multiplicity of gas outlet ports. The number of ports changes in the longitudinal direction of the bearing, in such a manner that the number of gas outlet ports in the bearing area of the bearing pad increases in the movement direction of the opposite bearing surface past the bearing pad.

The device according to the invention can be implemented on a CT scanner, but it can also be used in any other apparatus exhibiting a stationary gantry and a rotating gantry.

The inventive aerostatic bearing, which can be swiveled about one axis, about two axes, or about a center point of the sphere, and which has a bearing capacity that preferably changes over a longitudinal extent of the bearing pad, is not limited for use with CT scanners. To the contrary, it can be employed in any support mounting for fast-moving bodies such as, for example, for seating the rotors of other motors or generators.

The invention is explained in detail below on the basis of one example with reference to the drawings.

BRIEF DESCRIPTION OF THE DRAWINGS

FIG. 1 is a top plan view of a device according to the invention and is taken in the axial direction;

FIG. 2 is a cross-sectional detail of the device shown in FIG. 1 and is taken along the dotted line II-II;

DETAILED DESCRIPTION OF THE INVENTION

Figure 3:
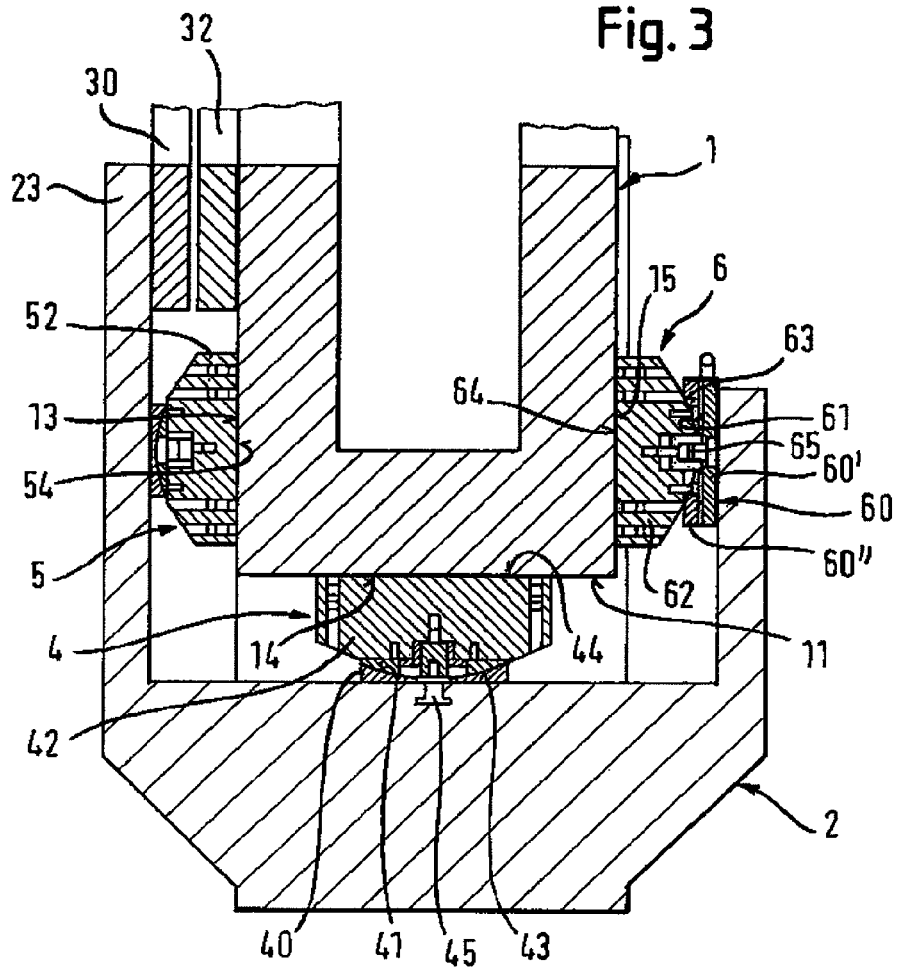
FIG. 3 is an enlarged view of detail III of FIG. 2.

FIGS. 1 and 2 show an inventive device, as implemented, for example, in a CT scanner. An annular rotating body 1 is arranged in the interior of a stationary body 2. The outer stationary body 2 can be the stationary gantry of a CT scanner, and the inner rotating body 1 can be the rotating gantry of a CT scanner, on which the imaging apparatus (not illustrated) of the CT scanner is mounted.

A first face side 20 of the stationary body 2 has three radial lands 23, 24, 25, which point radially inwards and which carry on their respectively radially inner ends an annular electric coil arrangement 30 of the axial electric direct drive 3.

On a first face side 10 of the rotating body 1 located opposite the coil arrangement 30 in the axial direction is an annular magnet arrangement 32 of the electric direct drive 3. Both the annular magnet arrangement 32 and the electric coil arrangement 30, which is also ring-shaped, are arranged coaxially to the axis of rotation (X) of the rotating body 1.

The device of the invention is vertically oriented so that the axis of rotation (X) extends horizontally. A first radial bearing 4 and a second radial bearing 4' are arranged on the stationary body so as to be offset by 45° in the circumferential direction to one side or to the other side of the lowest point of the inner circumference 21 of the stationary body 2 and form bearings that support the rotating body 1. Alternatively, the radial bearings 4, 4' can also be offset by 60° or another angle of less than 90° relative to the lowest point. In this context the first radial bearing 4 is located in the region of the first radial land 23, and the second radial bearing 4' is located in the region of the second radial land 24. The third radial land 25 is fixed on the highest point of the inner circumference 21 of the stationary body 2.

A third radial bearing 4" is provided at the lowest point of inner circumference 21 of the stationary body 2. This radial bearing is a radial balancing bearing which provides additional vertical support for the rotating body 1 on the stationary body 2.

Constructional details of the radial bearings 4, 4', 4" are provided in greater detail below.

Each of the three radial lands 23, 24, 25 of the stationary body 2 has an axial bearing 5, 5', 5" on the inside of the stationary body facing the rotating body 1. Each axial bearing has a bearing area facing the first face side 10 of the rotating body 1.

The construction of the axial bearings 5, 5', 5" is described in more detail below.

The second face side 22, which is positioned to face away from first face side 20 of stationary body 2, also has three radial lands 26, 27, 28, which point radially inwards and which are each located at the same circumferential position as the first radial lands 23, 24, 25, so that the respective lands 26, 27, 28 become aligned with the respective lands 23, 24, 25 when viewed in the axial direction. The second radial lands 26, 27 28 are shorter, when viewed in the radial direction, than the first radial lands 23, 24, 25.

Each of the second radial lands 26, 27, 28 has, located opposite the second face side 12 of the rotating body 1, an axial balancing bearing 6, 6', 6", the respective bearing area of which interacts with an opposing bearing area on the second face side 12 of the rotating body 1.

The construction of a radial support bearing 4, 4' will now be described below with reference to FIG. 3.

The respective radial bearings 4, 4' each comprise a bearing base 40 and a bearing pad 42. Base 40 is mounted on stationary body 2. At the side facing away from the stationary body 2 the bearing base 40 has a spherically concave surface 41. A surface 43 that is correspondingly curved in a spherically convex manner rests against concave surface 41 and is formed on the aft side of the bearing pad 42 that faces towards the bearing base 40. The side of bearing pad 42 that faces away from the convex surface 43 defines a bearing area 44. The bearing base 40 and the bearing pad 42 are connected together with a tension rod 45 in such a manner that it is possible for the bearing pad 42 to execute a swivel motion over a predefined angle on all sides about the common center point of the sphere of the concave surface 41 and the convex surface 43. The two curved surfaces 41 and 43 form a ball head bearing for the bearing pad 42.

The bearing area 44 exhibits a curvature, which is adapted to the curvature of the outer circumference 11 of the rotating body 1 in such a way that in the ideal state a uniformly wide bearing gap is formed between the bearing area 44 and the opposite bearing area 14, formed on the outer circumference 11 of the rotating body 1.

The ability of bearing pad 42 to swivel on all directions relative to stationary body 2, even if the axis of rotation (X) of the rotating body 1 is sloped relative to the central axis of the circular inner circumference 21 of the stationary body 2, makes sure that a bearing gap with a constant width between the bearing area 44 and the outer circumference 11 of the rotating body 1 is maintained. The unrestricted swivel capacity of the bearing pad 42 on all sides assures that a constant bearing gap is automatically attained.

The axial bearings 5, 5', 5" are constructed in the same way as the radial bearings 4, 4', so that the axial bearings 5, 5', 5" can also be swiveled in all directions. Only bearing area 54 of the respective axial bearings 5, 5', 5" is not curved, and instead is configured so as to be flat, in order to interact with the flat opposite bearing area 13 on the first face side 10 of the rotating body 1. In this case, too, the all around swivel capacity of the respective bearing pad 52 ensures that a constant width of the bearing gap will be automatically produced.

The axial balancing bearings 6, 6', 6" are provided with a corresponding swivel capacity on all sides, as was described above in connection with the radial bearings 4, 4' and the axial bearings 5, 5', 5". In addition, however, the axial balancing bearings 6, 6', 6" have respective bearing areas 64 which cooperate with an opposite bearing area 15, formed on the second face side 12 of rotating body 1, to enable movement between the respective bearing bases 60 and the respective bearing pads 62 in a direction that is perpendicular to its respective bearing area in the unswiveled state. Thus, the axial balancing bearings 6, 6', 6" not only have the capacity to swivel on all sides, the respective bearing pads 62 can additionally be moved towards the bearing base 60 or away from it.

The respective bearing pad 62 of the axial balancing bearing 6, 6', 6" is prestressed against the opposite bearing area, formed on the second face side 12 of the rotating body 1, by means of a spring force, a pneumatic force or a hydraulic force, in such a manner that the resulting prestresses balance the respective aerostatic bearing pressure of the axial balancing bearing, designed as an aerostatic bearing, as well as the opposite axial bearing, which is also designed as an aerostatic bearing. For this purpose, bearing base 60 is made of two parts. The first base part 60' is securely connected to the stationary body 2, and the second base part 60" has a concave surface 61, against which the convex surface 63 of the bearing pad 62 rests. The tension rod 65, connecting the bearing pad 62 to the bearing base 60, is configured as a piston cylinder unit, which not only holds the bearing pad 62 and the second base part 60" in close contact, but which also allows movement between the unit composed of bearing pad 62 and second base part 60" in relation to the first bearing part 60' in a direction perpendicular to the bearing areas 64, 15. In addition, the tension rod 65, designed as a piston cylinder unit, allows the bearing pad 62 to swivel about the center point of the sphere, as already described above in connection with the radial bearing 4.

The radial balancing bearing 4" is constructed in the same manner as the axial balancing bearings 6, 6', 6". However, the bearing pad of radial balancing bearing 4" is movable in relation to the bearing base in the radial direction. In this way the swivelable radial balancing bearing 4", which can be moved in the radial direction, supports the rotating body 1 together with the radial support bearings 4 and 4', but without causing a static redundancy of the radial support mounting of the rotating body 1.

The axial bearings 5, 5', 5" as well as the axial balancing bearings 6, 6', 6", the radial bearings 4, 4' and the radial balancing bearing 4" are configured as conventional aerostatic bearings. These aerostatic bearings have air discharge nozzles 46 in the form of micro holes in the respective bearing areas 44, 54, 64. These micro holes are conventionally cut into the bearing area as is known from the prior art by means of high energy radiation, such as, for example, by means of laser radiation, as is disclosed, for example, in DE 44 36 156 C1.

Figure 4:
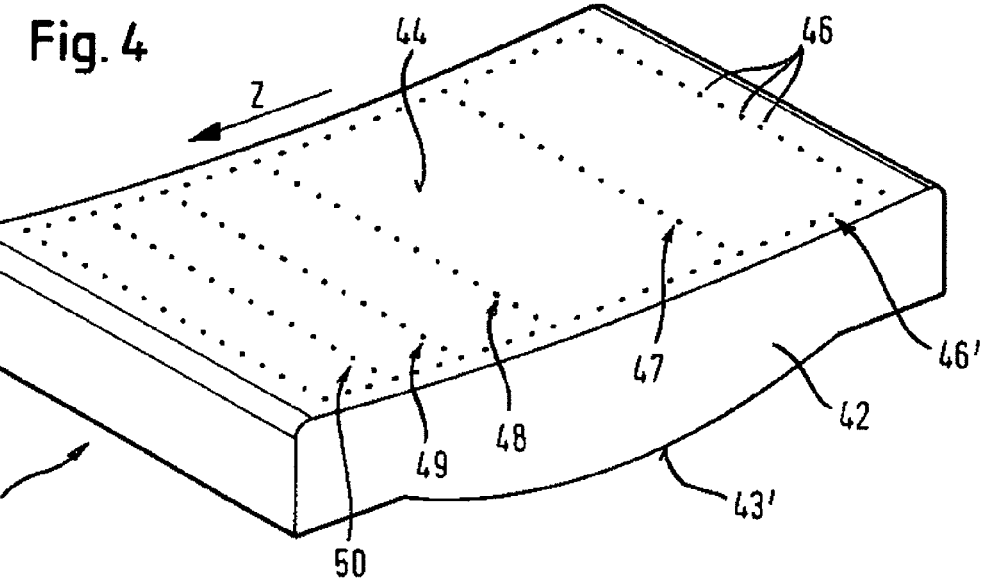
FIG. 4 is a perspective view of a bearing pad made in accordance with the present invention and having a load bearing capacity that changes in the longitudinal direction of the bearing pad.

FIG. 4 is a perspective view of one example of a bearing pad 42 with its bearing area 44. An especially advantageous embodiment of an aerostatic bearing is explained below. In the illustrated case, the bearing capacity increases in the longitudinal direction as indicated by arrow (Z) in FIG. 4. FIG. 4 shows very clearly that the air outlet nozzles 46 for the bearing air are arranged along the circumference of the bearing area 44 to form a rectangle 46' of nozzles that is parallel to the circumference. There are also rows 47, 48, 49, 50 of outlet nozzles for the bearing air and which are arranged at right angles to the longitudinal direction (Z). The distance between the respective rows 47, 48, 49, 50 decreases in the direction Z, so that the region of the bearing area 44 shown on the left front side of FIG. 4 has more air outlet nozzles per unit of area than the aft region shown on the right of FIG. 4. This increases the load bearing capacity of the bearing 4 in the region where there are more air outlet nozzles per unit of area. Thus, the bearing 4 shown in FIG. 4 has a bearing load carrying capacity that increases in the direction (Z).

If an opposite bearing surface (not illustrated in FIG. 4) moves past the bearing area 44 at a high speed in the direction Z, then the aft region of the bearing area 44 shown on the right in FIG. 4 attempts to lift off the opposite bearing area because the air near the surface moving with the opposite bearing area penetrates into the bearing gap. However, the higher load bearing capacity is generated in the front (left) region of the bearing 4, so that the higher bearing pressure caused by levered forces acting around the seat of the bearing pad 42 moves the aft region of the bearing area 44 back again towards the opposite bearing surface. As a result, the bearing gap is kept constant over the longitudinal extent of the bearing pad 42 (in the (Z) direction).

Although the example shown in FIG. 4 has been described as a radial bearing 4, the bearing pads 52, 62 of the axial bearings 5, 5', 5", the axial balancing bearings 6, 6', 6" and the radial balancing bearing 4" are provided with the same or a similar arrangement of air outlet nozzles over the longitudinal extent of the respective bearing area, so that there, too, the load carrying capacity of the bearing is increased in the direction of the opposite bearing area the latter moves by.

This special embodiment of the aerostatic bearing shown in FIG. 4 is not restricted to use with a device having a directly driven rotating body, for example a CT scanner. It can be employed whenever there is a high-speed relative movement between the bearing pad and the opposite bearing surface at which aerodynamic effects caused by the high-speed difference between the two opposite bearing surfaces tend to cant the bearing pad relative to the opposite bearing area moving past. Thus, the bearing pad does not have to be swivelable on all sides. It suffices if the bearing pad can be swiveled about an axis that runs parallel to the opposite bearing surface and at right angles to the direction of motion of the movable body having the opposite bearing surface, as shown, for example, in FIG. 4 by means of the cylindrically curved convex area 43' on the rear side of the bearing pad 42.

The invention is not limited to the above-discussed embodiments that are referred to merely to give a general description of the principles underlying the invention. Rather, within the scope of protection the device of the present invention can also include embodiments other than the ones described above. In this context the device can exhibit special features that constitute a combination of the respective individual features of the claims.

Reference numerals in the claims, the specification and the drawings serve only to facilitate a better understanding of the invention and should not be understood as limiting the scope of protection.

What is claimed is:

1. Apparatus having a directly driven rotating body including a first face side, a second face side opposite the first face side, and a circumference, radially seated on radial bearings in relation to a stationary body and axially seated relative to the stationary body, with aerostatic bearings providing axial support mounting between the first face side and the stationary body, wherein the directly driven rotating body includes an annular magnet arrangement asymmetrically arranged on the first face side with respect to the second face side, which is configured coaxial relative to an axis of rotation of the rotating body, and the stationary body has at least one electric coil arrangement located opposite the annular magnet arrangement in the axial direction and defines with the annular magnet arrangement components of an electrical direct drive for the rotating body such that in use attractive forces are present between the annular magnet arrangement and the at least one electric coil arrangement to forcibly support the aerostatic bearings between the first face side and the stationary body, the stationary body is formed by a rotating gantry of the imaging apparatus, and, the rotating body is formed by a rotating gantry of the imaging apparatus.

2. Apparatus according to claim 1, wherein the rotating body is configured in the shape of a ring.

3. Apparatus according to claim 1, wherein the radial bearings are formed by aerostatic bearings.

4. Apparatus according to claim 1, including on the second face side at least one additional aerostatic axial bearing that has at least one bearing pad movable in a direction parallel to the axis and prestressed against the second face side of the rotating body by means of a spring force, a pneumatic force or a hydraulic force.

5. Apparatus according to claim 1, including at least one additional aerostatic radial bearing positioned below the rotating body and having at least one bearing pad that can be moved in the radial direction and that pushes against an outer periphery of the rotating body by means of a spring force, a pneumatic force or a hydraulic force.

6. Apparatus according to claim 1, including at least one additional aerostatic axial bearing for the first face side of the rotating drive, the at least one additional aerostatic axial bearing having at least one bearing pad that can be moved in a direction parallel to the axis and that is prestressed against the first face side of the rotating body by means of a spring force, a pneumatic force or a hydraulic force.

7. Apparatus according to claim 1, wherein at least one part of the axial bearings has at least one swivelable bearing pad that can be swiveled about a first axis that is perpendicular to the axis of rotation of the rotating body.

8. Apparatus according to claim 7, wherein the respective swivelable bearing pad can be swiveled about a second axis that is perpendicular to a plane spanned by the first axis and the axis of rotation.

9. Apparatus according to claim 7, wherein the swivelable bearing pad has a ball head bearing and is freely swivelable.

10. Apparatus according to claim 7, wherein the bearing pads are configured to increase a bearing capacity of the bearing in the direction of motion of an opposite bearing surface of the rotating body moving past at least one of the bearing pads.

11. Apparatus according to claim 10, including a multiplicity of gas outlet ports in a bearing area of the bearing pad which increases in the direction in which the opposite bearing surface of the rotating body moves past the bearing pad.

12. Apparatus according to claim 1, wherein at least one part of the radial bearings includes at least one swivelable bearing pad adapted to be swiveled about the first axis that is parallel to the axis of rotation of the rotating body.

13. Apparatus according to claim 12, wherein the respective swivelable bearing pad can be swiveled about a further, second axis that is parallel to a tangent of the periphery of the rotating body.

14. Apparatus according to claim 12, wherein the swivelable bearing pad includes a ball head bearing to render it freely swivelable.

15. Apparatus according to claim 1, wherein the imaging apparatus is a stationary gantry of a CT scanner.

16. Apparatus according to claim 1 including at least one bearing pad, wherein the at least one bearing pad is adapted to be swiveled about a first axis which is at a right angle to the main movement direction and parallel to an opposite bearing surface of the rotating body and wherein the bearing pad is configured so that a bearing capacity of the bearing pad increases in the movement direction of the opposite bearing surface, moving past the bearing pad.

* * * * *